US010176587B2

(12) United States Patent
Takahashi et al.

(10) Patent No.: US 10,176,587 B2
(45) Date of Patent: Jan. 8, 2019

(54) MEDICAL CROSS-SECTIONAL IMAGE DISPLAYING APPARATUS AND METHOD FOR DISPLAYING CROSS-SECTIONAL IMAGE

(71) Applicant: Akita Prefectural Hospital Organization, Akita (JP)

(72) Inventors: Noriyuki Takahashi, Akita (JP); Tomomi Ohmura, Akita (JP)

(73) Assignee: Akita Prefectural Hospital Organization, Akita (JP)

( * ) Notice: Subject to any disclaimer, the term of this patent is extended or adjusted under 35 U.S.C. 154(b) by 157 days.

(21) Appl. No.: 15/421,825

(22) Filed: Feb. 1, 2017

(65) Prior Publication Data

US 2017/0249749 A1 Aug. 31, 2017

(30) Foreign Application Priority Data

Feb. 25, 2016 (JP) .................................. 2016-033721
Oct. 31, 2016 (JP) .................................. 2016-212403

(51) Int. Cl.
*G06K 9/00* (2006.01)
*G06T 7/37* (2017.01)
(Continued)

(52) U.S. Cl.
CPC ................ *G06T 7/37* (2017.01); *A61B 5/055* (2013.01); *A61B 5/4504* (2013.01);
(Continued)

(58) Field of Classification Search
CPC . A61B 2576/026; A61B 5/055; A61B 5/4504; A61B 5/7257; A61B 5/742;
(Continued)

(56) References Cited

U.S. PATENT DOCUMENTS

2005/0165294 A1* 7/2005 Weiss ..................... A61B 6/032
600/410
2008/0188741 A1* 8/2008 Mallya ................... A61B 6/032
600/426
(Continued)

FOREIGN PATENT DOCUMENTS

JP          2015034779 A       2/2015

*Primary Examiner* — Tom Y Lu
(74) *Attorney, Agent, or Firm* — Alix, Yale & Ristas, LLP

(57) ABSTRACT

The present invention provides an apparatus for displaying a two-dimensional cross-sectional image of an arbitrary base plane which matches to the subject's head without creating extra labor to the operator even when the subject's head is asymmetrical. The apparatus is connected to a display unit for displaying a cross-sectional image of a head. The apparatus comprising: a conversion parameter obtaining unit for obtaining a conversion parameter indicating a difference in shape between a standard head and a subject's head based on a volume data; a subject base plane generating unit for generating an anatomical base plane of the subject's head based on the conversion parameter and an anatomical base plane of the standard head; and a cross-sectional reconstruction unit for generating a cross-sectional image of the anatomical base plane of the subject's head based on the volume data of the subject's head and displaying said cross-sectional image on the display unit.

19 Claims, 12 Drawing Sheets

(51) Int. Cl.
*A61B 5/00* (2006.01)
*A61B 6/03* (2006.01)
*G06T 3/00* (2006.01)
*G06T 3/60* (2006.01)
*G06T 11/00* (2006.01)
*A61B 5/055* (2006.01)
*A61B 6/00* (2006.01)

(52) U.S. Cl.
CPC ............ *A61B 5/7257* (2013.01); *A61B 5/742* (2013.01); *A61B 5/743* (2013.01); *A61B 5/7435* (2013.01); *A61B 6/03* (2013.01); *A61B 6/032* (2013.01); *A61B 6/501* (2013.01); *A61B 6/505* (2013.01); *A61B 6/5217* (2013.01); *A61B 6/5223* (2013.01); *G06T 3/0068* (2013.01); *G06T 3/60* (2013.01); *G06T 11/006* (2013.01); *A61B 6/465* (2013.01); *A61B 6/466* (2013.01); *A61B 2576/026* (2013.01); *G06T 2207/20048* (2013.01); *G06T 2207/30016* (2013.01); *G06T 2210/41* (2013.01)

(58) Field of Classification Search
CPC ......... A61B 5/743; A61B 5/7435; A61B 6/03; A61B 6/032; A61B 6/465; A61B 6/466; A61B 6/501; A61B 6/505; A61B 6/5217; A61B 6/5223; G06T 11/006; G06T 2207/20048; G06T 2207/30016
See application file for complete search history.

(56) References Cited

U.S. PATENT DOCUMENTS

| | | | |
|---|---|---|---|
| 2009/0116708 A1* | 5/2009 | Kim | A61B 6/463 382/128 |
| 2010/0040264 A1* | 2/2010 | Volkau | A61B 6/5235 382/128 |
| 2011/0004450 A1* | 1/2011 | Mishelevich | A61N 2/006 703/2 |
| 2012/0230566 A1* | 9/2012 | Dean | G06T 19/00 382/131 |
| 2016/0098832 A1* | 4/2016 | Yoo | G06T 7/0012 382/131 |
| 2016/0155226 A1* | 6/2016 | Kano | A61B 5/055 382/131 |
| 2017/0024888 A1* | 1/2017 | Ishii | G06T 7/0016 |
| 2017/0143430 A1* | 5/2017 | Miga | A61B 34/20 |
| 2017/0206654 A1* | 7/2017 | Shiroishi | G06T 7/0012 |

* cited by examiner

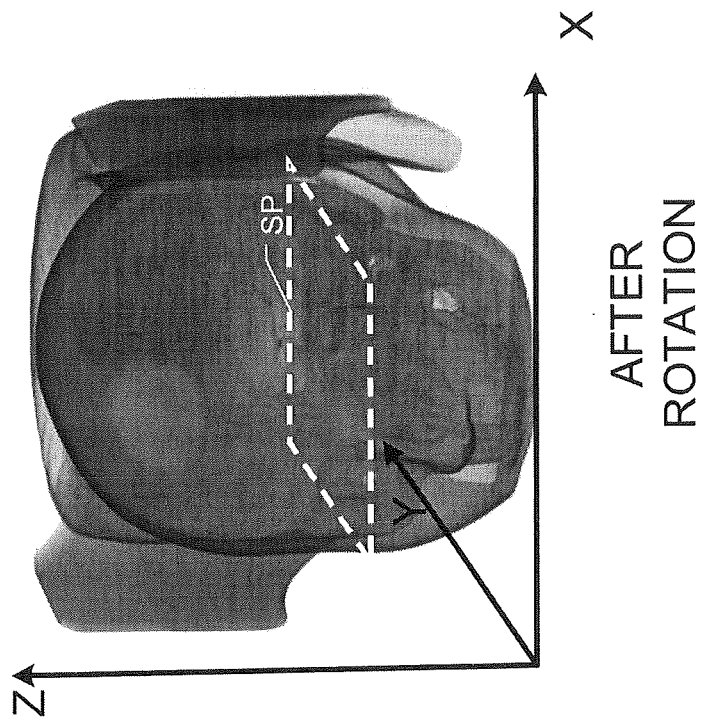
FIG. 7B  AFTER ROTATION
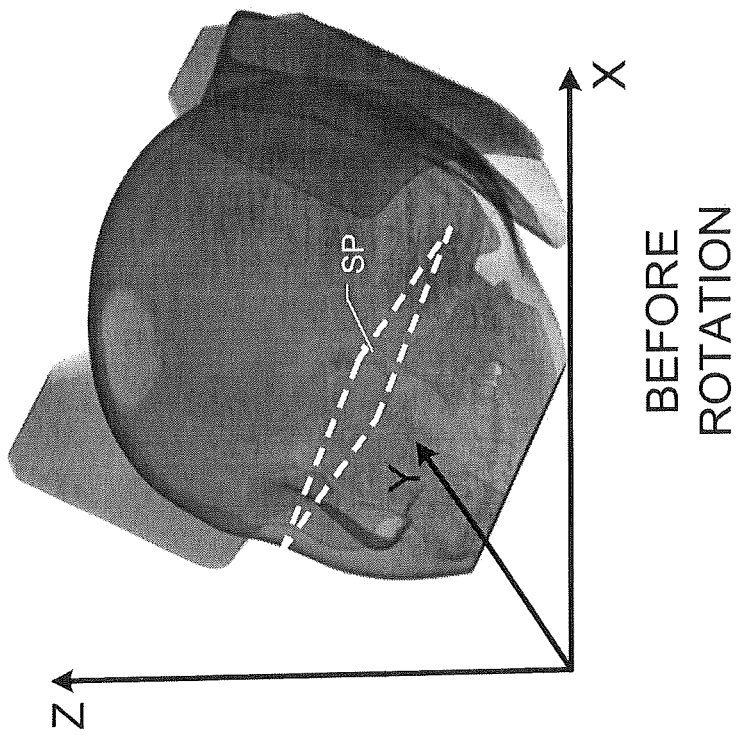
FIG. 7A  BEFORE ROTATION

MEDICAL CROSS-SECTIONAL IMAGE DISPLAYING APPARATUS AND METHOD FOR DISPLAYING CROSS-SECTIONAL IMAGE

CROSS-REFERENCE TO RELATED APPLICATION

This application claims priority to and the benefit of Japan Patent Application No. 2016-033721, filed on Feb. 25, 2016, and Japan Patent Application No. 2016-212403, filed on Oct. 31, 2016, in the Japan Patent Office, the disclosure of which are incorporated herein by reference in their entireties.

FIELD

The present invention relates to a cross-sectional imaging using a tomographic imaging apparatus such as an X-ray CT (computer tomography) apparatus, an MRI (magnetic resonance imaging) apparatus or a nuclear medicine imaging apparatus such as SPECT (Single Photon Emission Computed Tomography) or PET (Positron Emission Tomography) apparatus. Particularly, the present invention relates to a medical cross-sectional image display apparatus and a method for displaying cross-sectional images of an appropriate base plane using volume data of subject's head obtained from the tomographic imaging apparatus.

DESCRIPTION OF THE RELATED ART

In order to obtain a reconstructed image of multiple cross-sections from a three-dimensional head image data acquired by a tomographic imaging apparatus, the operator is required to define a base plane visually by changing cross-sectional images in three directions (axial plane, sagittal plane and coronal plane) during a multiplanar reconstruction. Particularly, in the captured three-dimensional image, since the shape of the head differs from subject to subject, the three-dimensional image of the subject's head is slanted or rotated in relation to the coordinate axis of the apparatus, thus requiring the operator to make manual corrections. Also, difficulty in setting a base plane visually created dispersions in base plane setting among operators.

Japanese Unexamined Patent Publication No. 2015-034779 A1 discloses a method for setting a base plane in the three-dimensional head image, including the steps of projecting array of light along sideline of subject's head using a projector which emits a linear beam from a device attached onto the tomographic imaging apparatus, obtaining a position information of a top board on which a subject is placed, and obtaining a base plane of a three-dimensional head image from both information.

However, since the shape of the subject's head is generally asymmetrical, the method of imaging a tomographic image disclosed in '779 is incapable of providing a reconstructed image of multiple cross-sections with no slants on left and right sides. This method requires the operator to perform extra commands during the process, thus requiring extra time for diagnosis.

The present invention provides a medical cross-sectional image display apparatus and method for displaying a cross-sectional image for displaying a two-dimensional cross-sectional image of an arbitrary base plane without creating extra labor to the operator even when the subject's head is asymmetrical.

SUMMARY

One aspect of the present invention relates to a medical cross-sectional image display apparatus connected to a display unit for displaying a cross-sectional image of a head. The medical cross-sectional image display apparatus comprising: a conversion parameter obtaining unit for obtaining a conversion parameter indicating a difference in shape between a standard head and a subject's head based on a volume data of the standard head and the subject's head; and the subject base plane generating unit for generating an anatomical base plane of the subject's head based on the conversion parameter and an anatomical base plane of the standard head. The apparatus further comprises a cross-sectional reconstruction unit for generating a cross-sectional image of the anatomical base plane of the subject's head based on the volume data of the subject's head and displaying said cross-sectional image on the display unit.

Another aspect of the present invention relates to a medical cross-sectional image display apparatus further comprising a normal base plane generating unit for generating the anatomical base plane of the standard head. The normal base plane generating unit generates the normal base plane by inputting a standard voxel value to the voxel of the standard base plane out of a three-dimensional voxel data of the standard head.

In one aspect of the present invention, the conversion parameter is a linear transformation, a nonlinear transformation, an affine transformation or a Fourier transform, in which an error between the voxel value of the volume data of the subject's head and the voxel value of the volume data of the standard head becomes minimum.

In one aspect of the present invention, the subject's head and the standard head includes at least one of a cerebral parenchyma, cranium bones and skin of facial parts outside of the cranium bones.

Another aspect of the present invention is that, the medical cross-sectional image display apparatus further comprises an angle adjusting unit for calculating angles between two axial directions of a plane of the medical cross-sectional image display apparatus and the anatomical base plane of the subject's head, rotating the anatomical base plane of the subject's head based on the angle and matching the anatomical base plane of the subject's head on the surface of the medical cross-sectional image display apparatus.

The medical cross-sectional image display apparatus further comprises a cross-sectional edge setting unit for setting a first edge and a second edge of a region for reviewing the cross-sectional image based on the volume data of the subject's head. The anatomical base plane includes a plane surface including an orbitomeatal line (OM LINE) connecting the orbital center and a center of the external auditory meatus, a plane surface including a supraorbitomeatal line (SM line) connecting a supraorbital margin and a center of the external auditory meatus and an infraorbitomeatal plane connecting an edge of the external auditory meatus and infraorbital margin.

The cross-sectional image is applicable for MRI (magnetic resonance imaging), SPECT (Single Photon Emission Computed Tomography) image or PET (Positron Emission Tomography) image.

The second aspect of a present invention is a method for displaying a cross-sectional image of a head on the display unit using a medical cross-sectional display apparatus connected to the display unit. The method comprises: a step for obtaining a conversion parameter indicating a difference between a standard head and a subject's head based on a volume data of the standard head and the subject's head; and a step for subject base plane generating an anatomical base plane of the subject's head based on the conversion parameter and an anatomical base plane of the standard head. The method further comprises a step for generating a cross-sectional image on the display unit by generating the cross-sectional image of the anatomical base plane of the subject's head based on the volume data of the subject's head.

The medical cross-sectional display apparatus and the method allows to display a two-dimensional cross-section image of arbitrary base plane corresponding to the subject's head without creating extra labor to the operator.

BRIEF DESCRIPTION OF THE DRAWINGS

FIG. 7A is an image before rotating a three-dimensional image of a subject's head.

FIG. 7B is an image after rotating a three-dimensional image of a subject's head.

DETAILED DESCRIPTION

This embodiment is explained using the X-ray CT apparatus as reference. However, the cross-section display apparatus may be applied in a same manner for other medical tomographic imaging apparatuses such as MRI apparatus and PET apparatus.

Schematic Description of X-ray CT Apparatus and Structure of the Apparatus

Figure 1:
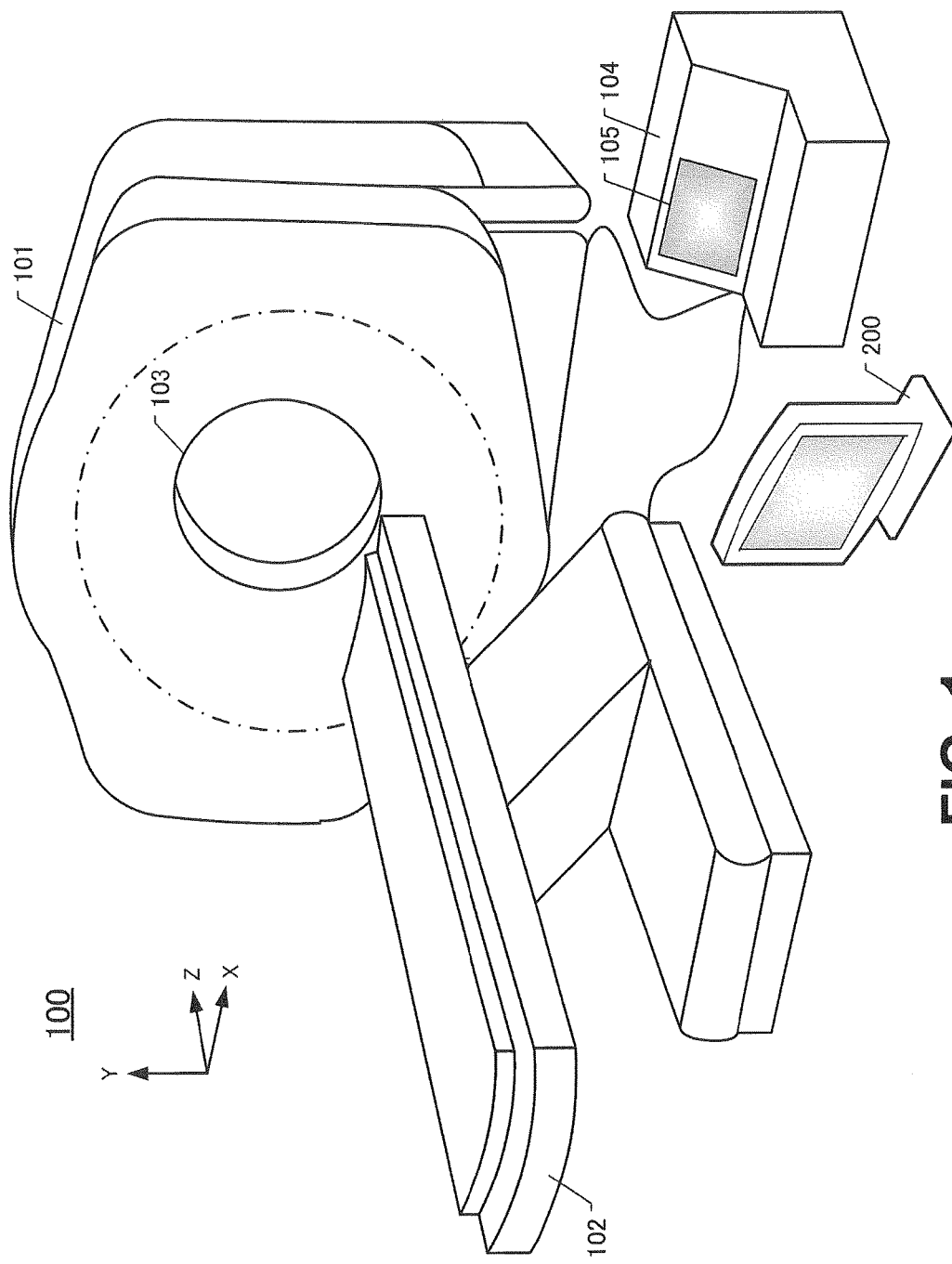
FIG. 1 is a schematic diagram illustrating an appearance of the X-ray CT apparatus 100.

FIG. 1 is a schematic diagram illustrating an outer appearance of the X-ray CT apparatus 100. As shown in FIG. 1, the X-ray CT apparatus 100 comprises a scan gantry 101 for collecting projecting data using a detecting unit by performing an X-ray scan to a subject and a cradle 102 for situating a subject and moving in and out of a bore 103 where the images are captured. Additionally, the X-ray CT apparatus 100 further comprises an operation console 104 for operating an X-ray CT apparatus 100 and reconstructing the three-dimensional image based on a projecting data collected by the detecting unit.

In FIG. 1, the body-axis direction of the subject is referred to as Z-axis, the direction perpendicular to the ground is referred to as Y-axis and a plane direction orthogonal to the Y-axis and Z-axis is referred to as X-axis.

The cradle 102 has an internal motor embedded therein for moving the cradle 102 horizontally and vertically. Then, the subject is situated on the cradle 102 for moving in and out of the bore 103 of the scan gantry 101.

The operation console 104 includes an input unit for receiving input from an operator and a monitor for displaying an image. The operation console 104 further comprises: a central processing unit (CPU) for controlling each component necessary for collecting projection data of the subject and reconstructing the three-dimensional image; a data acquisition buffer for collecting data obtained by the scan gantry 101; and a storage unit for storing information such as program and data. The operation console 104 includes an input unit such as keyboard and a display unit 105. The display unit 105 displays a reconstructed three-dimensional image or an MPR (Multi Planar Reconstruction) of an arbitrary image.

A medical image processing workstation 200 may be connected to the operation console 104. The medical image processing workstation 200 image-processes an MPR images.

Figure 2:
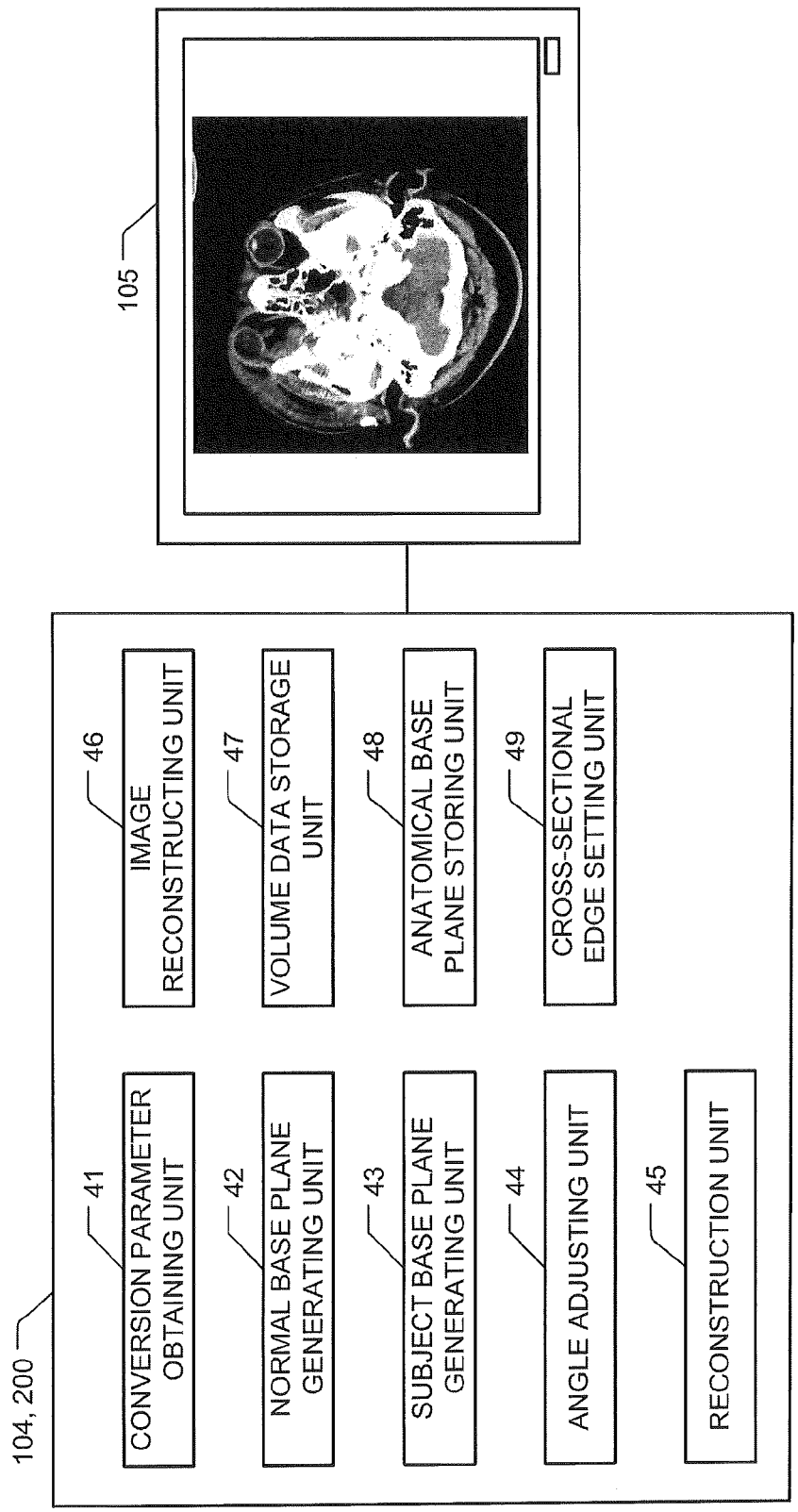
FIG. 2 is a block diagram explaining an operation console 104.

FIG. 2 is a block diagram illustrating an operation console 104 or a medical image processing workstation 200 connected to the display unit 105. As shown in FIG. 2, the CPU of the operation console 104 or medical image processing workstation 200 includes a conversion parameter obtaining unit 41, a normal base plane generating unit 42 and a subject base plane generating unit 43. The CPU of the operation console 104 or the medical image processing workstation 200 comprises an angle adjusting unit 44, a cross-section reconstruction unit 45, an image reconstructing unit 46 and a cross-sectional edge setting unit 49. Furthermore, the storage unit of the operation console 104 or medical image processing workstation 200 includes a volume data storage unit 47 and an anatomical base plane storing unit 48.

The conversion parameter obtaining unit 41 obtains a conversion parameter indicating a difference in a shape between standard size head and subject's head based on the volume data of subject's head and the volume data of standard size head. The volume data of standard size head is averaging scanned data which is obtained by scanning several hundred to several thousand heads using the X-ray CT apparatus. The volume data of head includes a volume data of cerebral parenchyma, a volume data of cranium bones and a volume data of visible organs (such as facial parts including eyes, ears, nose, mouth and scalp) of a standard subject. The operator may generate the volume data of standard head or may obtain the volume data which is available for free, may store them in the storage unit.

The volume data of standard head is generally a data obtained by averaging the volume data of adult's head, but the volume data of standard head for infant (less than one year's old) may also be prepared separately. Additionally, the volume data of standard head for child (between one year's old and preliminary school child) may also be prepared separately.

The conversion parameter is a parameter used in the transfer function for minimizing the difference between the voxel value of the volume data of the subject's head and the voxel value of the volume data of the standard head. A linear transformation such as affine transformation, a nonlinear transformation or a Fourier transform may be used as a transfer function. Furthermore, a combined transfer function of a linear transformation function and a nonlinear transformation function is also applicable.

For example, when an affine transformation is applied to a transfer function, the conversion parameter obtaining unit 41 obtains a conversion parameter used for the affine transformation in order to minimize the measurement error between the voxel value of the volume data of subject's cerebral parenchyma and voxel value of the volume data of standard size cerebral parenchyma. At least one of a cerebral parenchyma, cranium bones or skin may be used as the volume data of the head. Additionally, the volume data of a combination of two or more of the cerebral parenchyma, cranium bones or skin may be used.

The normal base plane generating unit 42 generates an anatomical base plane of the standard head. The anatomical base plane includes a plane surface including an orbitomeatal line (OM LINE) connecting the orbital center and a center of the external auditory meatus, a plane surface including a supraorbitomeatal line (SM line) connecting a supraorbital margin and a center of the external auditory meatus and an infraorbitomeatal plane connecting an edge of the external auditory meatus and infraorbital margin. The anatomical base plane includes a coronal plane and a sagittal plane. Such anatomical base planes may include head organs i.e. brain, sinus cavity and orbital region.

The subject base plane generating unit 43 generates the anatomical base plane of the subject's head based on the conversion parameter obtained by the conversion parameter obtaining unit 41 and the anatomical base plane of the subject's head.

An angle adjusting unit 44 adjusts angle of the anatomical base plane of the subject's head to the XY-plane, XZ-plane or YZ-plane of the X-ray CT apparatus 100. The angle is adjusted so that the operator may easily view the cross-sectional image on the display unit 105. It is not mandatory to adjust angle of the subject's head to the anatomical base plane if the operator does not find discomfort in viewing the image.

The cross-section reconstruction unit 45 generates a cross-sectional image on the anatomical base plane of the subject's head based on the volume data of the subject's head and displays the image on the display unit 105.

The image reconstructing unit 46 reconstructs the three-dimensional CT image based on the projecting data obtained by the detecting unit.

The volume data storage unit 47 stores the volume data generated based on the projecting data of the subject's head obtained by the detecting unit.

The anatomical base plane storing unit 48 stores the anatomical base plane of the standard head generated by the normal base plane generating unit 42. Once one or a plurality of anatomical base planes are stored, it is unnecessary for the normal base plane generating unit 42 to generate the anatomical base plane of the subject's head every time the subject's head image is captured.

The cross-sectional edge setting unit 49 sets a region of the axial plane of the subject's head in the Z-axis direction. This means, the cross-sectional edge setting unit 49 sets an upper edge and a lower edge of a region where the operator needs to diagnose by viewing the axial plane image. If the operator needs to view sagittal plane of the head for diagnosis, the cross-sectional edge setting unit 49 determines the left edge and right edge of the head, and if the operator needs to view the coronal plane of the head, the cross-sectional edge setting unit 49 determines the front edge of the head (close to nose) and the rear edge of the head (back side of the head).

Operation of the Apparatus

Figure 3:
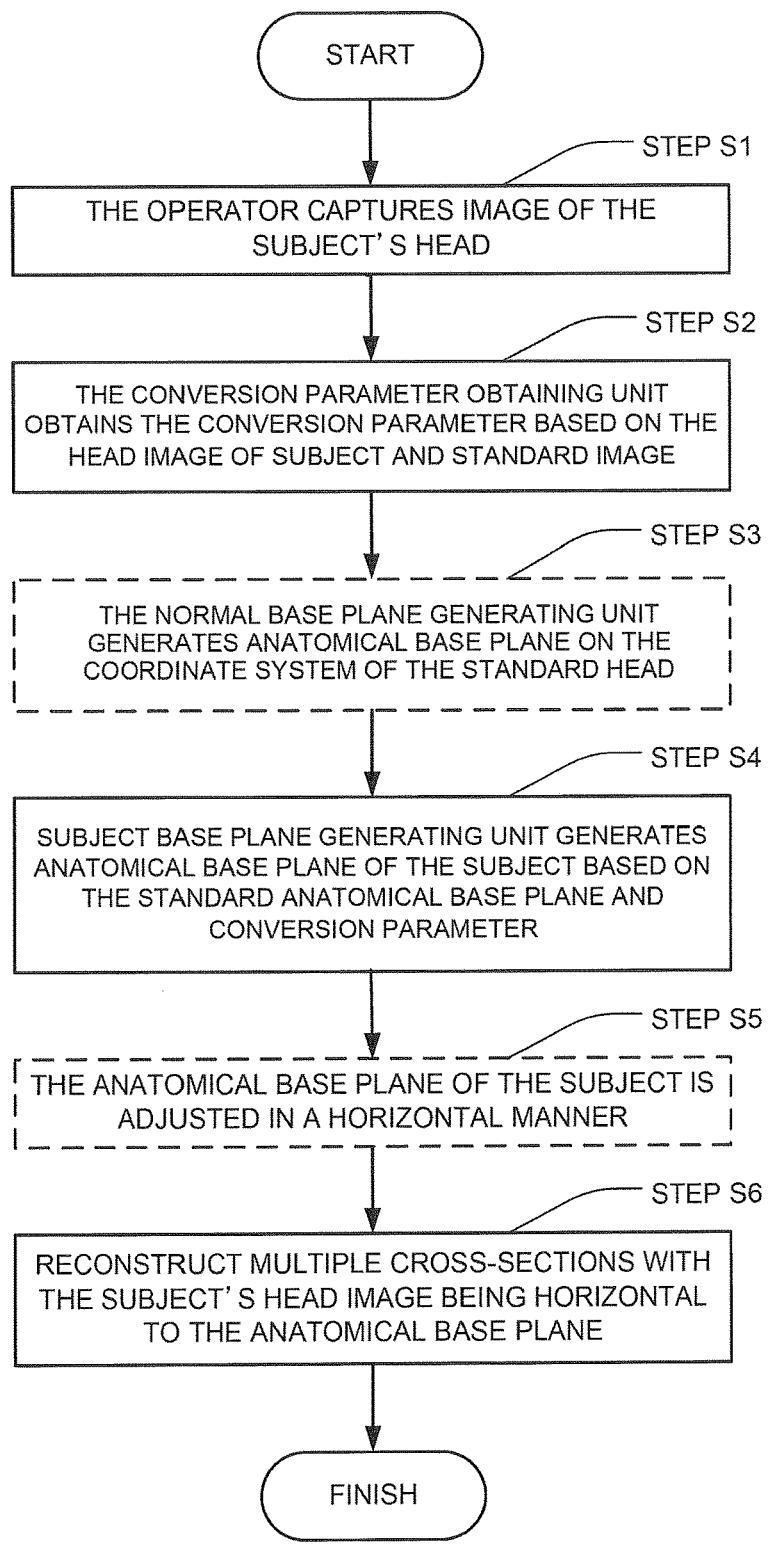
FIG. 3 is a flowchart for displaying a two-dimensional cross-sectional image corresponding to an arbitrary anatomical base plane.

FIG. 3 is a flowchart for displaying a two-dimensional cross-sectional image in correspondence to the arbitrary anatomical base plane. In the explanation of the flowchart, the anatomical base plane is a plane including the orbitomeatal line (BP or SP). This embodiment explains the operation console 104 displaying a cross-sectional image of the appropriate base plane. However, it is possible to have the medical image processing workstation 200 perform the steps S2 to S6 mentioned below to display a cross-sectional image of the appropriate base plane.

In step S1, the operator captures an image of the subject's head situated on the cradle 102. Then, the volume data storage unit 47 stores the volume data generated by the projecting data obtained by the detecting unit.

The operator may also capture the image in a wide range, such as an image from head to chest or the image from head to leg. In this case, the CPU of the operation console 104 automatically detects the volume data of the head. For example, the CPU detects the start position of the volume data of the subject's head to 30 cm away from the start position of the head. Another method for detecting the head is that, when the cross-sectional area calculated by the volume data of the subject reduces from more than 200 cm$^2$ to less than 200 cm$^2$ and then becomes more than 200 cm$^2$, the CPU determines that the area less than 200 cm$^2$ as neck of the subject and determines that a distance between the start position of the volume data to the neck as the head.

In step S2, the conversion parameter obtaining unit 41 obtains the conversion parameter of the transformational function for determining a difference in shape between the subject's head and standard head based on the volume data of the subject and the volume data of the subject's head.

Steps S3 to S6 illustrates steps for obtaining the cross-sectional images of the axial plane of the head. The steps for obtaining the cross-sectional images of sagittal plane and coronal plane of the head are omitted since the fundamental steps are similar regardless of the direction.

Figures 4A, 4B:
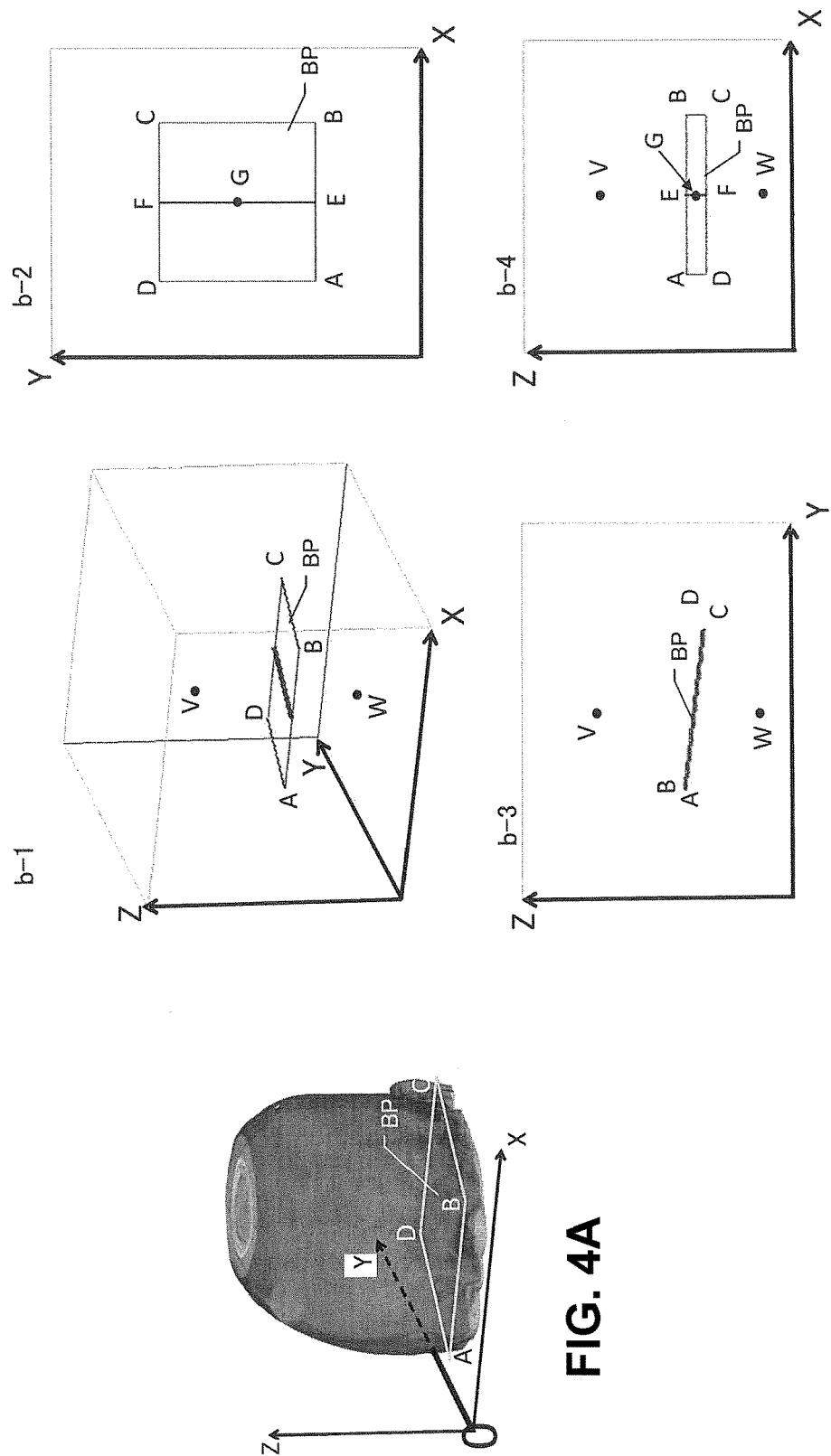
FIG. 4A is a diagram illustrating coordinate systems of X-ray CT apparatus 100 on the three-dimensional image of a standard head.
FIG. 4B is an exemplary diagram illustrating a setting of plane surface including OM line relative to the standard head.

In step S3, the normal base plane generating unit 42 generates the anatomical base plane of the standard head (plane including a orbitomeatal line). FIGS. 4A and 4B show a method for generating a plane including the orbitomeatal line on the standard head using the normal base plane generating unit 42.

FIG. 4A is a diagram illustrating the coordinate axis of the X-ray CT apparatus. The axial direction of a subject situated on the cradle 102 is denoted as Z-axis. FIG. 4B (b-1) is a schematic diagram of the plane surface including the orbitomeatal line (OM line) set onto the standard head, (b-2) is a plan view of the XY-axis plane, (b-3) is a plan view of the YZ-axis plane and (b-4) is a plan view of the XZ-axis plane.

Method for Generating Normal Base Plane Surface

In one example, the normal base plane generating unit 42 displays the three-dimensional image of the standard head in a manner as described in FIG. 4A, on the display unit 105 and displays the indicating image on the display unit 105 for inputting four points on the OM line. The operator inputs the points A, B, C and D using the input device such as a mouse on the three-dimensional image of the standard head in order to generate a plane BP including the orbitomeatal line (OM LINE). The points A, B, C and D becomes the plane BP including the orbitomeatal line (OM LINE).

Each diagram in FIG. 4B illustrates the position of four points A, B, C and D on the three-dimensional coordinate axis. Other than the CT value, the normal base plane generating unit 42 inputs the predetermined voxel value (200 for example) for each voxel on the straight line connecting between points A to B, points B to C, points C to D and points D to A. The plane BP including the orbitomeatal line of the standard head is set. The plane BP including the orbitomeatal line of the standard head is distinguishable from other voxel value.

The plane BP including the orbitomeatal line of the standard head is stored in the anatomical base plane storing unit 48. When imaging the head of another subject, the plane BP including the orbitomeatal line may be unloaded from the anatomical base plane storing unit 48 without having to generate the plane BP including the orbitomeatal line on the normal base plane generating unit 42.

The normal base plane generating unit 42 calculates a midpoint E disposed between points A and B and a midpoint F disposed between points C and D, and inputs predetermined voxel value (300 for example) along a straight line connecting midpoints E and F. This sets the rotating axis EF of a plane including the orbitomeatal line of the standard head. The rotating axis EF is distinct from other voxel values. This rotational axis EF is used when the angle adjusting unit 44 adjusts the angle of plane BP including the orbitomeatal line of the subject's head to the XY-axis plane of the X-ray CT apparatus 100. Instead of using the rotational axis EF, the rotational axis BD of a straight line connecting points B and C or a straight line connecting points A and D may be used.

Furthermore, the normal base plane generating unit 42 calculates a center point G of the rotational axis EF. The center point G is a central point of the plane BP including the orbitomeatal line. The normal base plane generating unit 42 inputs a predetermined voxel value (400 for example) on the center point G. The center point G provides distinction from other voxel values. The center point G is used so as to situate the center point G in a center of the display unit 105 when the cross-section reconstruction unit 45 generates the cross-sectional image on the plane BP including the orbitomeatal line of the subject and displays the image on the display unit 105.

Although not described in FIG. 4A, the operator may input the points V and W to the three-dimensional image using the input unit. The points V and W in FIG. 4B indicate upper edge and lower edge of the three-dimensional image of the standard head. The points V and W indicates range of the Z-axis direction for the cross-section reconstruction unit 45 to reconstruct the transverse image of multiple cross-sections parallel to the plane SP including the orbitomeatal line of the subject. In other words, points V and W indicate the region in the Z-axis direction of the subject's head which are set by the operator for diagnosing on a necessary basis.

When the operator sets the points V and W to the three-dimensional image of the standard head, the points V1 and W1 are automatically set to the three-dimensional image of any subject's head. The method for cross-sectional edge setting unit 49 automatically setting the points V1 and V1 to each subject will be explained later using FIG. 11 as reference in case of not setting the points V and W to the three-dimensional image of standard head.

Figure 5:
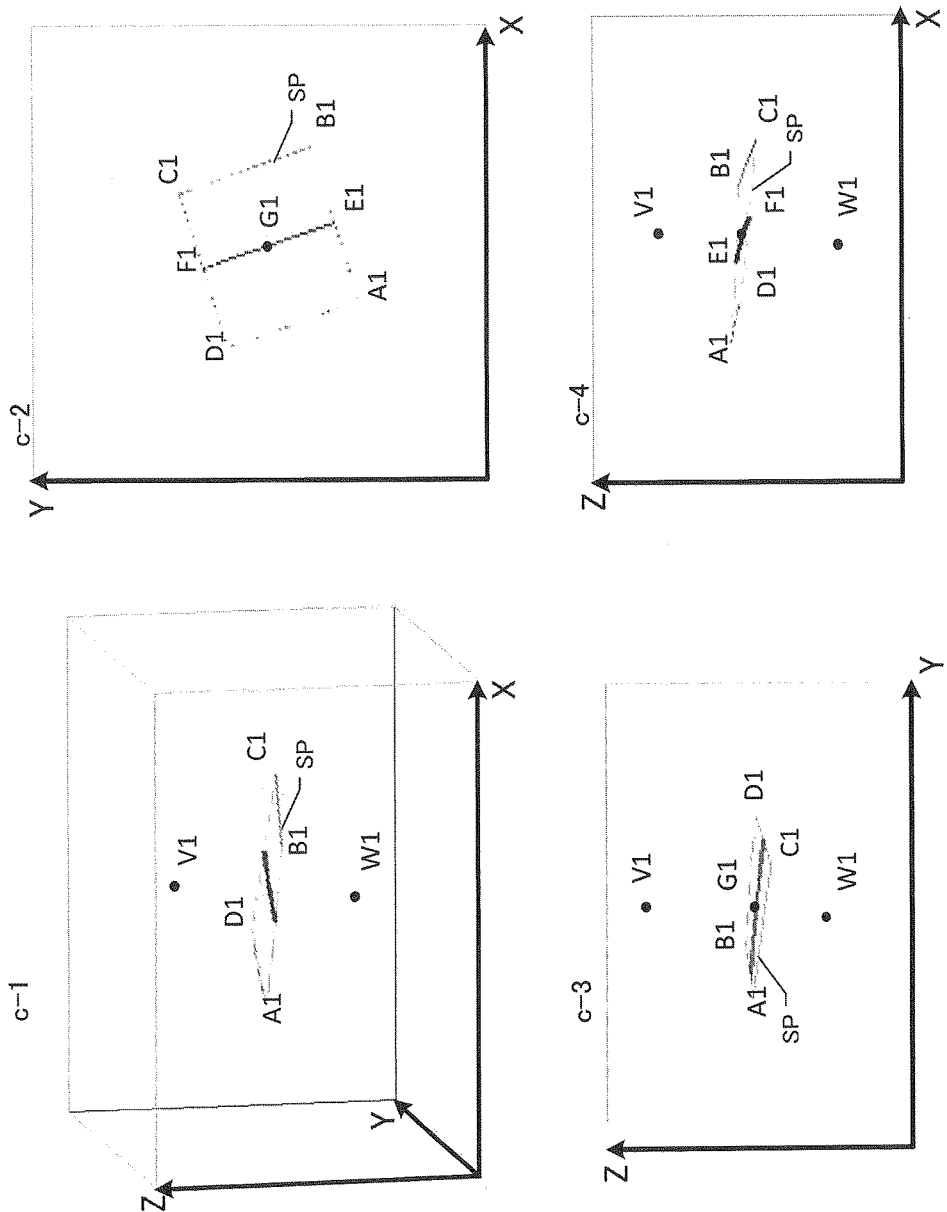
FIG. 5 is a diagram illustrating a situation of generating an anatomical base plane on a head of a subject.

Going back to the flowchart of FIG. 3, in step S4, the subject base plane generating unit 43 generates the plane SP including orbitomeatal line of the subject's head based on the conversion parameter obtained during the step S2 and the plane BP including the orbitomeatal line of the subject's head. FIG. 5 (c-1) to (c-4) indicates the subject base plane generating unit 43 generating the plane SP including the orbitomeatal line on the subject's head. Each of FIG. 5 (c-1) to (c-4) indicates points A1, B1, C1, D1, midpoints E1 and F1, center point G1, upper edge V1 and lower edge W1 generated by using the conversion parameter acquired by the linear transformation during the step S2. For the conversion parameter acquired by the affine transformation during step S2, the subject base plane generating unit 43 affine-transforms the conversion parameter used for obtaining the plane BP including the orbitomeatal line and generates the plane SP including the orbitomeatal line of the subject's head. The transfer function used during step S4 is a same transfer function as used during the step S2.

Going back to the flowchart in FIG. 3, in step S5, the angle adjusting unit 44 matches the coordinate axis (XY-axis plane) of the X-ray CT apparatus 100 and the plane SP including the orbitomeatal line of the subject's head. Since this embodiment is explained using the plane SP including the orbitomeatal line, the angle is matched to the XY-axis plane. However, angle should be matched to the XZ-axis plane if the anatomical base plane is a coronal surface trespassing the nasal cavity, and the angle should be matched to the YZ-axis plane if the anatomical base plane is a sagittal surface trespassing the orbital region.

Figure 6:
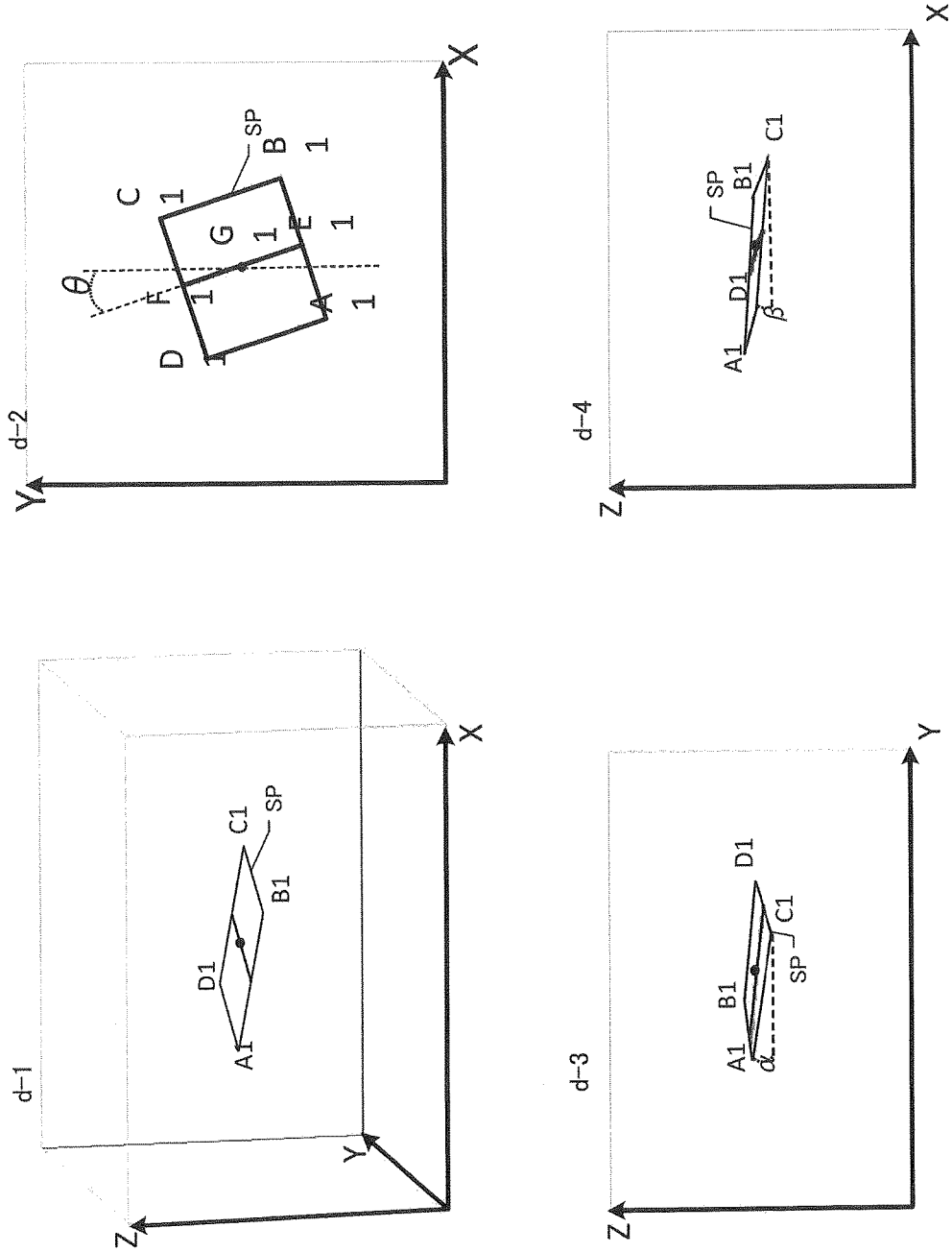
FIG. 6 is a diagram illustrating the rotational angles α, β and θ of an anatomical base plane on a head of the subject.

The angle adjusting unit 44 first determines an angle of the plane SP and horizontal plane XY including the orbitomeatal line of the subject's head. Each of the diagram d-1 to d-4 of FIG. 6 corresponds to the diagram c-1 to c-4 of FIG. 5, with points V1 and W1 eliminated from FIG. 6 and angle θ, angle α and angle β are newly added. In d-2 of FIG. 6, the angle adjusting unit 44 calculates the angle between a straight line connecting midpoints E1 to F1 and the Y-axis. Furthermore, the angle adjusting unit 44 calculates the angle α between plane SP including orbitomeatal line of subject's head and X-axis and the angle β between the plane SP including orbitomeatal line of subject's head and Y-axis.

If the transfer function used in step S4 is an equation of the linear transformation, the plane SP including the orbitomeatal line of the subject's head is a flat plane. However, if the transfer function used in step S4 is a nonlinear transformation, the plane SP including the orbitomeatal line of the subject's head is a curved plane. This creates difficulty in calculating the angles θ, α and β. In this case, the angle adjusting unit 44 assumes a flat plane by approximating the curved plane SP including the orbitomeatal line by using the three-dimensional least square method (Z=aX+bY+c) and calculates the angles θ, α and β based on coefficients a, b and c. The angle adjusting unit 44 assumes the straight line connecting the midpoints E1 to F1 using the two-dimensional least square method (Y=dX+e) from the curved line connecting the midpoints E1 to F1 on the plane SP including the orbitomeatal line, and calculates angle θ based on coefficients d and e. Other method is that, the angle adjusting unit 44 calculates the angles θ, α and β by calculating the integral value at a predetermined point on a plane SP including the orbitomeatal line formed as a curved plane.

Next, angle adjusting unit 44 rotates the three-dimensional image of the subject's head based on angles θ, α and β. Strictly, the angle adjusting unit corrects position for each angle to the volume data; however, the explanation is made based upon the rotation of three-dimensional image for providing better understanding of invention. By rotating the three-dimensional image, the facial side faces forward and the plane SP including the orbitomeatal line becomes flat. FIG. 7A is an image before rotating the three-dimensional image of subject's head, and FIG. 7B is an image after rotating the three-dimensional image of subject's head. Accordingly, the angle adjusting unit 44 matches the XY-axis plane of the X-ray CT apparatus 100 and plane SP including the orbitomeatal line of subject's.

By performing angle adjustment as described in step S5, the subject's facial parts face forward when displayed on the display unit 105 and the plane SP including the orbitomeatal line aligns horizontally to the display, thus providing fine view to the operator. However, if slanted view of the subject's facial part does not give discomfort to the operator, the angle adjustment in step S5 may be omitted or angle θ do not need to be rotated.

Figure 8A:
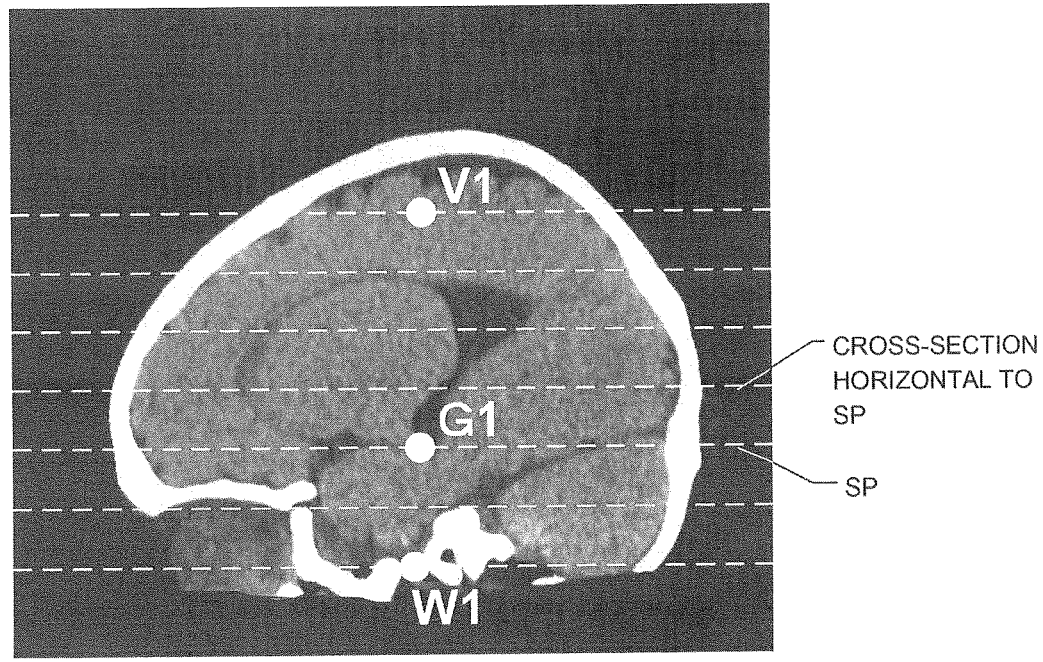
FIG. 8A is a diagram indicating positions of evenly-spaced multiple cross-sections along the sagittal plane of subject's head.
Figure 8B:
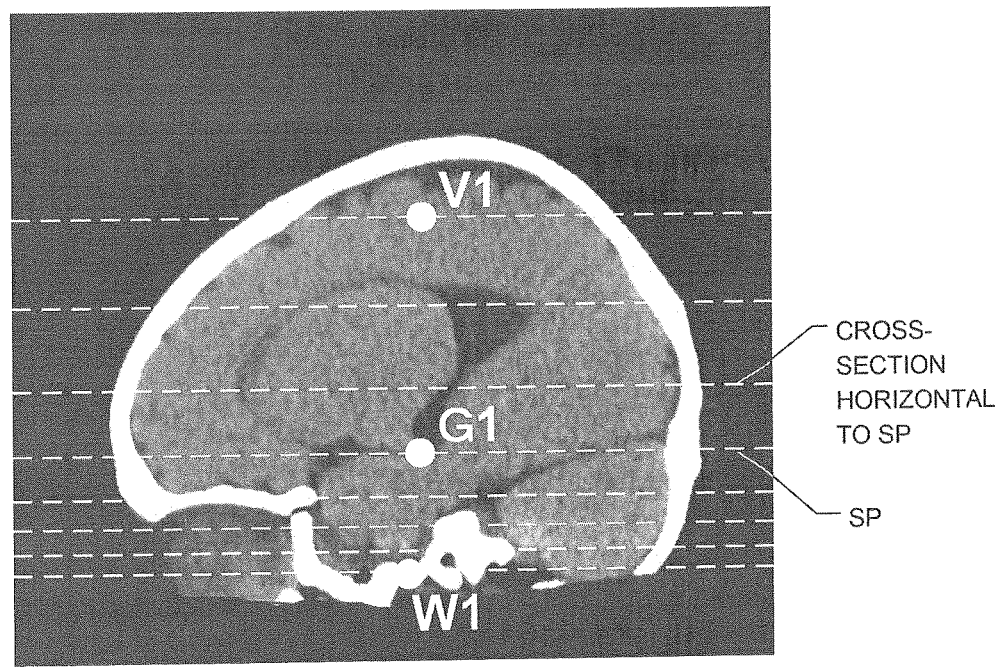
FIG. 8B is a diagram indicating a position of the multiple cross-sections along the sagittal plane of subject's head with spaces gradually decreasing as it reaches closer to W1.

Going back to the flowchart in FIG. 3, in step S6, the cross-section reconstruction unit 45 generates the cross-sectional image on the plane SP including the orbitomeatal line of the subject's head based on the volume data of the subject's head. Then, the cross-section reconstruction unit 45 displays the cross-sectional image on the display unit 105. The operator inputs a thickness and distance of the axial plane using the input unit beforehand. For example, when the operator inputs 10 mm as thickness and evenly-spaced as distance, the cross-section reconstruction unit 45 generates the plane SP including the orbitomeatal line of subject's head and multiple cross-sectional images parallel to the plane SP from the upper edge points V1 to the lower edge point W1. FIG. 8A is a diagram indicating evenly-spaced multiple cross-sections on the sagittal plane of subject's head. If the operator sets the distance as gradually decreasing from 20 mm to 3 mm, the cross-section reconstruction unit 45 generates the plane SP including the orbitomeatal line of subject's head and cross-sectional images parallel to the plane SP from upper edge V1 to lower edge W1. As shown in FIG. 4B, the upper edge V1 and lower edge W1 are the regions in which the operator determined as necessary regions for diagnosis. FIG. 8B is a diagram indicating a position of the multiple cross-section with gradual spaces on the sagittal plane of subject's head.

Alternative Method 1 of Normal Base Plane

In the above-mentioned embodiment, the operator inputted the corner points A, B, C and D of a rectangular shape to the three-dimensional image of the standard head and generated the plane BP including the orbitomeatal line (OM line).

In the alternative embodiment 1, the normal base plane generating unit 42 displays the two-dimensional stereoscopic image of the sagittal plane of the standard head and inputs two points of the orbitomeatal line (OM line).

Figure 9A:
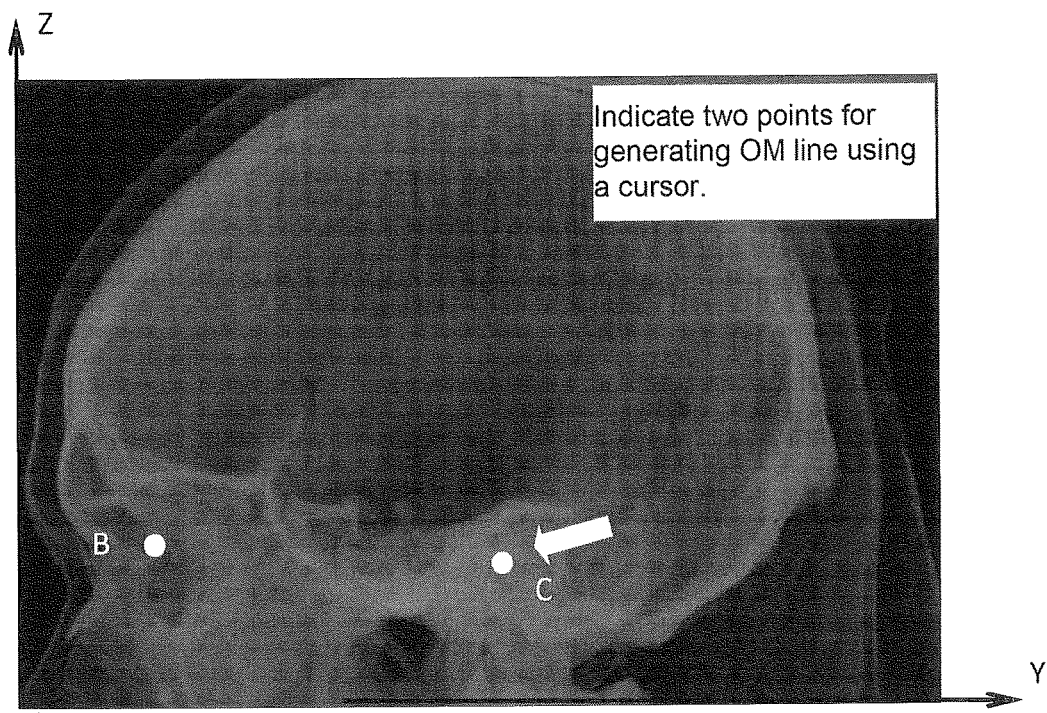
FIG. 9A is a diagram illustrating coordinate system of X-ray CT apparatus 100 relative to the two-dimensional image of standard head.
Figure 9B:
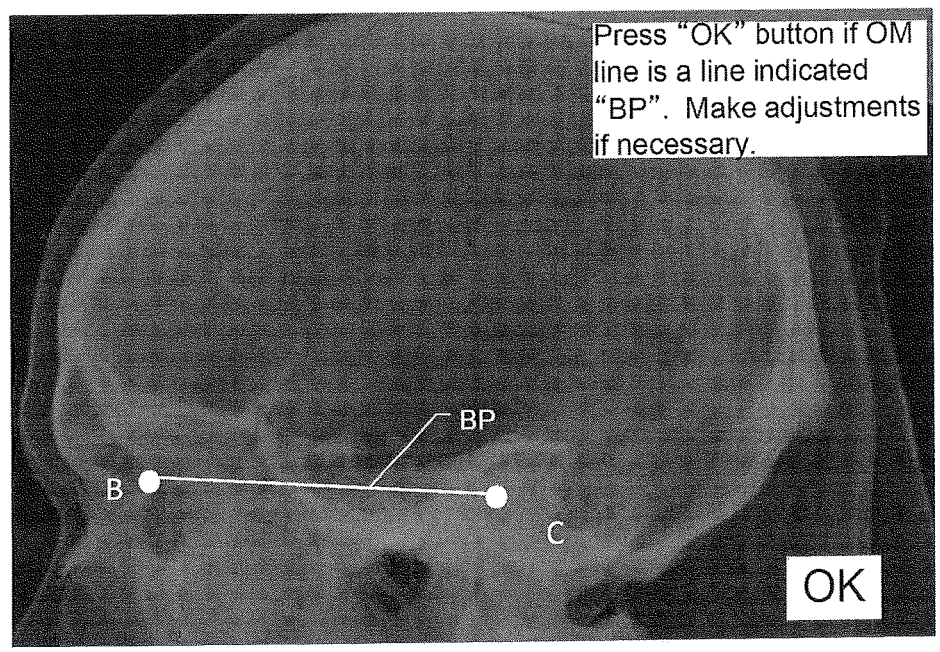
FIG. 9B is a schematic diagram illustrating a setting of a plane surface including orbitomeatal line (OM LINE).

FIG. 9A is a two-dimensional stereoscopic image of a sagittal plane of the standard head displayed on the display unit 105. The normal base plane generating unit 42 commands the operator to input points B and C forming the orbitomeatal line (OM line) on the two-dimensional stereoscopic image of the sagittal plane of the standard head. FIG. 9B is a diagram of the normal base plane generating unit 42 drawing the plane BP including the orbitomeatal line (OM line) on the two-dimensional stereoscopic image of the sagittal plane of the standard head. If the operator finds no problem with the generated plane BP (the plane being straight line for two-dimensional image in FIG. 9B), the operator clicks "OK" button.

Next, the normal base plane generating unit 42 moves the points B and C in a predetermined distance in X-axis direction for forming points A and D, thereby generating the plane BP including the orbitomeatal line (OM line). As explained in FIG. 4B, the normal base plane generating unit 42 calculates the rotational axis EF and midpoint G of the rotational axis EF.

Alternative Method 2 of Normal Base Plane

The plane BP including the orbitomeatal line (OM line) generated by using the normal base plane generating method and the alternative method was a rectangular-shaped. However, the plane BP is not limited to the rectangular shape.

Figure 10A:
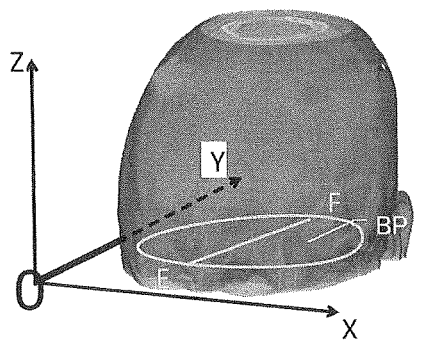
FIGS. 10A and 10B are diagrams illustrating a setting of elliptical plane surface including orbitomeatal line (OM line) to the three-dimensional image of standard head.
Figure 10B:
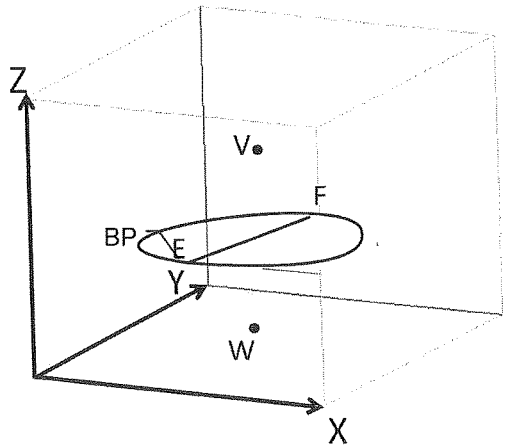

FIGS. 10A and 10B illustrate a situation of the operator setting the starting point E and ending point F of the longitudinal axis of the ellipse indicated on the three-dimensional image of the standard head displayed on the display unit 105. The points E and F form a longitudinal axis of the ellipse and a rotational axis EF as explained in the FIG. 4B. The normal base plane generating unit 42 illustrates an ellipse with the short axis being 0.6 to 1.0 times the length of the longitudinal axis, wherein 1.0 times length forms a perfect circle. As illustrated in FIG. 9, the normal base plane generating unit 42 may command the operator to input points E and F of the orbitomeatal line (OM line) to the two-dimensional stereoscopic image on the sagittal plane of the standard head.

Figure 10C:
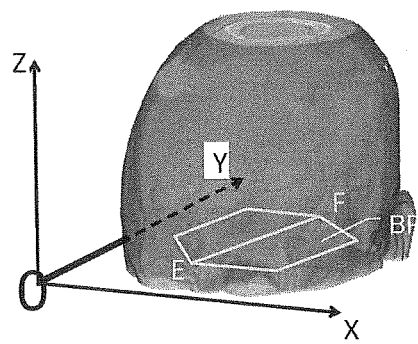
FIGS. 10C and 10D are diagrams illustrating a setting of hexagonal plane surface including orbitomeatal line (OM line) to the three-dimensional image of a standard head.
Figure 10D:
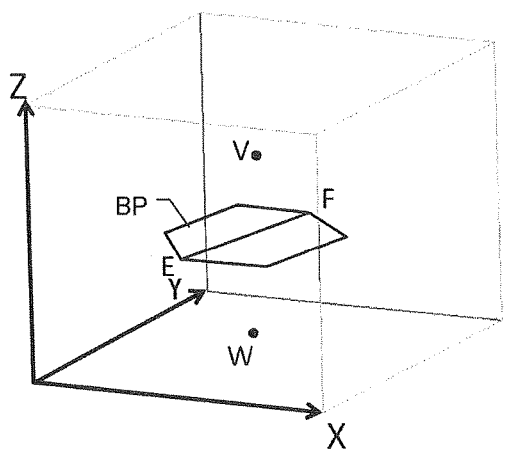

FIGS. 10C and 10D illustrate a situation of the operator setting the orthogonal points E and F of the hexagon to the three-dimensional image of the standard head displayed on the display unit 105. The points E and F are longitudinal axis of the hexagon and a rotational axis EF as explained in the FIG. 4B. As illustrated in FIG. 9, the normal base plane generating unit 42 may command the operator to input points E and F of the orbitomeatal line (OM line) on the two-dimensional stereoscopic image on the sagittal plane of the standard head.

Figure 10E:
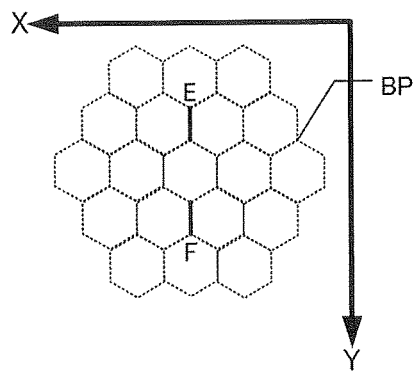
FIG. 10E is a diagram indicating the midpoints E and F set to a XY-plane surface comprising a plurality of hexagonal planes.

FIG. 10E is a diagram illustrating the points E and F set onto a XY-plane formed by a plurality of hexagons. When the operator sets points E and F on the three-dimensional image of the standard head displayed on the display unit 105, multiple hexagons with a size smaller than hexagons indicated in FIG. 10C and plane PB including orbitomeatal line (OM line) are formed. When multiple hexagons are formed on the plane, the number of line data increases, thus enhances the preciseness when calculating the plane using the maximum square method.

Automatic Setting of V1 and W1 Points

In FIGS. 4A and 4B, the operator sets the points V and W within the range of the Z-axis direction of the standard head for automatically setting the points V1 and W1 within a range of the subject's head in the Z-axis direction. The method for the cross-sectional edge setting unit 49 automatically setting the points V1 and W1 within the range of the subject's head in the Z-axis direction is explained hereinbelow.

Figure 11:
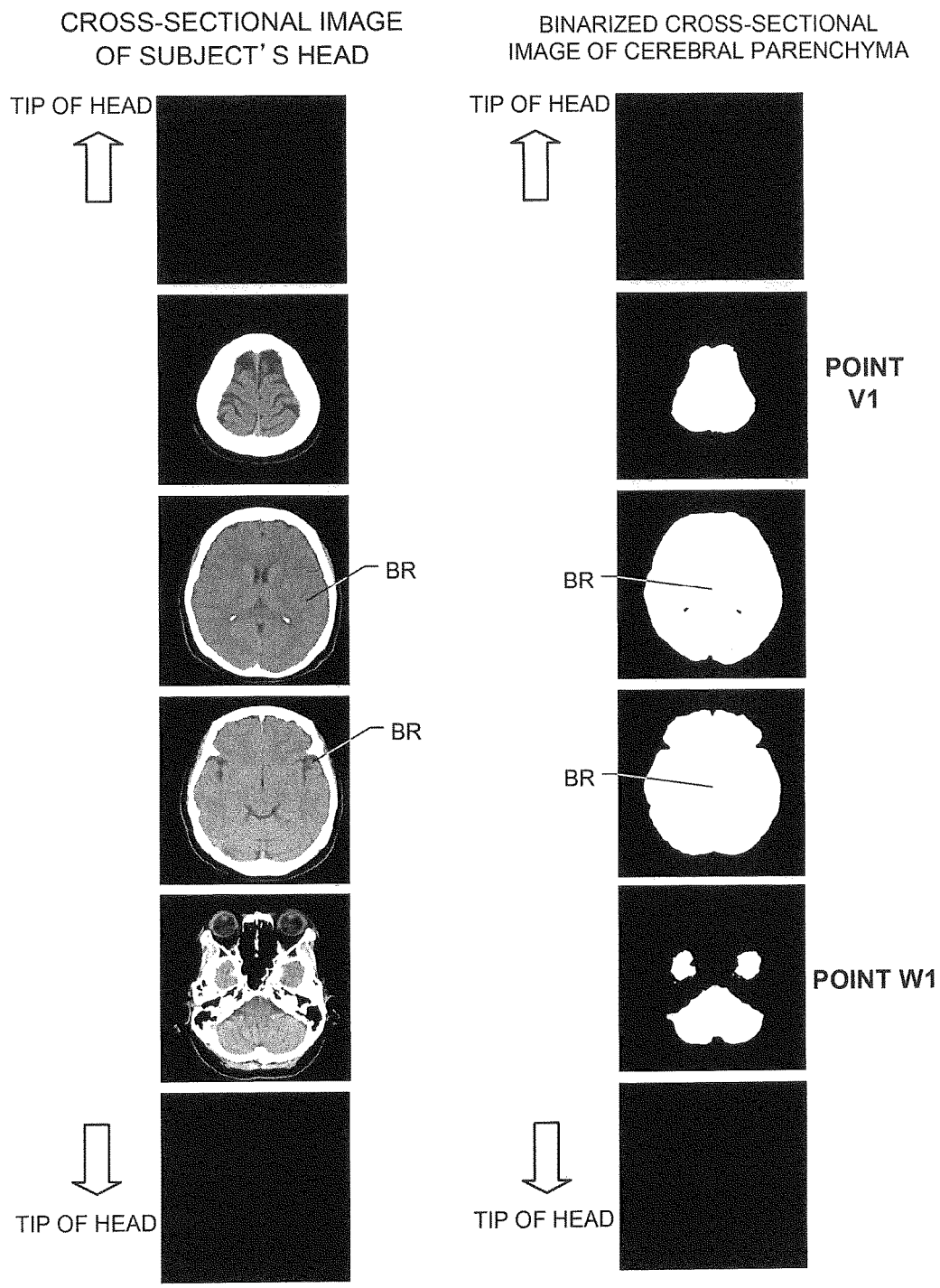
FIG. 11 is a diagram illustrating a set of axial plane images of the subject's head based on the volume data and the binarized image of the axial plane image.

The left side image of FIG. 11 is an axial image from the tip of the head to the neck based on the volume data of subject's head. The right side image of FIG. 11 is a binarized image of the cerebral parenchyma on the axial plane image.

The cross-sectional edge setting unit 49 reconstructs image of the plurality of axial plane images of the tip of the head to the neck based on the volume data of the subject's head. As shown in left-side diagram, a region BR indicated with grayscale is the axial plane image of the cerebral parenchyma. Although FIG. 11 displays only six axial plane images, several hundreds to several thousands of axial plane images are generated from the volume data.

Next, the cross-sectional edge setting unit 49 removes the cranium bones from the reconstructed axial plane image. As indicated in the left-side image of FIG. 11, the reconstructed cranium bones are displayed in white color due to high CT value. Accordingly, the cross-sectional edge setting unit 49 removes the cranium bone region by processing with threshold value. Next, the cross-sectional edge setting unit 49 removes the CT image (small area region) located outside of the cranium bones. This means that skins located outside of the cranium bones are removed from the image. Then, the cross-sectional edge setting unit 49 binarizes the remaining region with threshold value, image-processes the cerebral parenchyma in white color and image-processes the remaining region with black color. The right-side diagram is binarized image with the region BR of cerebral parenchyma indicated with white color. The cross-sectional edge setting unit 49 calculates the area of the white brain region and sets the point V1 at a point where the region of the cerebral parenchyma reaches to, for example, 5 cm² while increasing the white region of the cerebral parenchyma. Furthermore, the cross-sectional edge setting unit 49 sets the point W1 at a point where the region of the cerebral parenchyma reaches to, for example, 10 cm² while decreasing the white region of the cerebral parenchyma.

Based on this embodiment, even when the operator with little experience images the head of the subject, the operator is able to display the image of the anatomical base plane and the plane horizontal to the base plane of the subject's head on the display unit without assistance from other operators.

Figure 12A:
FIG. 12A is a cross-sectional image of subject's head around the orbitomeatal line of the subject before applying the embodiment of this invention.
Figure 12B:
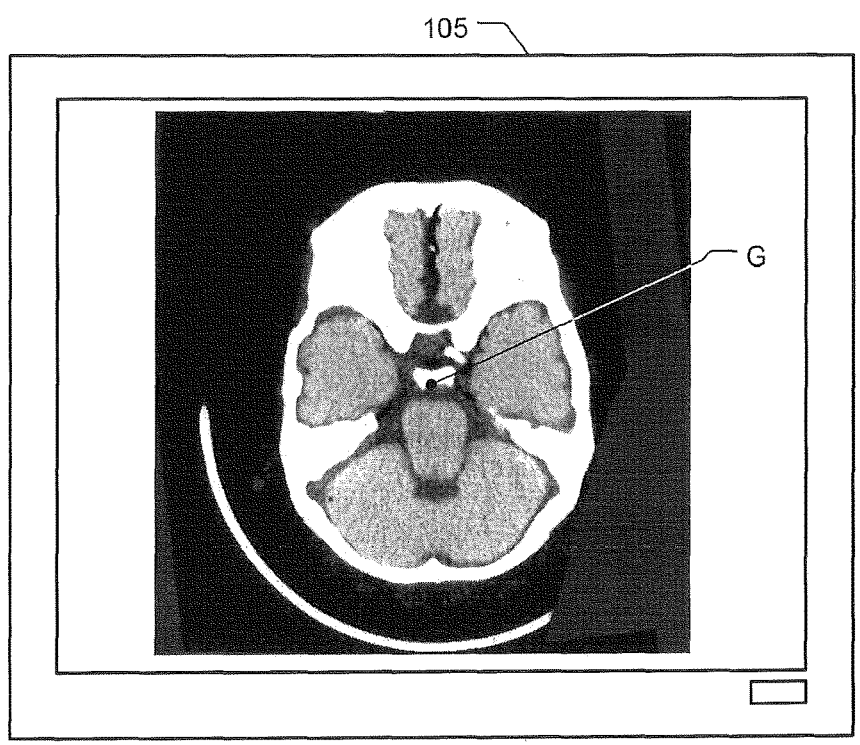
FIG. 12B is a cross-sectional image of the plane SP parallel to the orbitomeatal line of subject's head which is automatically adjusted by using the embodiment of present invention based on the volume data for imaging (A).

FIG. 12A is a cross-sectional image around the orbitomeatal line of the subject before applying the embodiment of this invention. The cross-sectional image is captured asymmetrically without taking the anatomical base plane in consideration. In FIG. 12A, the plane SP including the orbitomeatal line is not accurately displayed on the display unit 105. This occurs when the operator with little experience images the subject's head or when imaging the subject with head having highly asymmetrical shape. FIG. 12B is a cross-sectional image displayed on the display unit 105, wherein the cross-sectional image is parallel to the plane SP including the orbitomeatal line of the subject's head based on the volume data for imaging the FIG. 12A. The center point G of the cross-sectional image is positioned in center of the display unit 105. This allows the operator to easily diagnose the head of the subject.

The best-mode embodiment of the present invention has been explained in full detail; however, the person skilled in art may alter the embodiment within the scope of the present invention. As explained previously, this invention is applicable not only to the X-ray CT apparatus but also to the MRI apparatus, PET apparatus or SPECT apparatus. As disclosed in JP unexamined patent application No. 2012-189362, an apparatus for correcting the radiation absorption of the PET image or SPECT image using the CT data for enhancing the preciseness of image, which is available at market. The apparatus with PET and CT function, the apparatus with SPECT and CT function, the apparatus with PET and CT function or the apparatus with MRI and CT function may be used on the same coordinate system. By applying the embodiment of the present invention to the CT apparatus explained in this embodiment, the cross-sectional image corresponding to the base plane may be acquired for PET image, SPECT image or MRI image.

DESCRIPTION OF REFERENCE NUMERALS

BP . . . Anatomical Base Plane of Standard Head
SP . . . Anatomical Base Plane of Subject's Head
41 . . . Conversion Parameter Obtaining Unit
42 . . . Standard Base Plane Generating Unit
43 . . . Subject Base Plane Generating Unit
44 . . . Angle Adjusting Unit
45 . . . Cross-sectional Image Reconstruction Unit
46 . . . Image Reconstruction Unit
47 . . . Volume Data Storage Unit
48 . . . Anatomical Base Plane Storage Unit
100 . . . X-ray CT Apparatus
101 . . . Scan Gantry
102 . . . Cradle
103 . . . Bore
104 . . . Operation Console
Point V . . . Upper Edge of Sagittal Image of Standard Head
Point W . . . Lower Edge of Sagittal Image of Standard Head
Point V1 . . . Upper Edge of Sagittal Image of Standard Head
Point W1 . . . Lower Edge of Sagittal Image of Standard Head

What is claimed is:

1. A medical cross-sectional image display apparatus connected to a display unit for displaying a cross-sectional image of a head, comprising:
   a conversion parameter obtaining unit for obtaining a conversion parameter indicating a difference in shape between a standard head and a subject's head based on a volume data of the standard head and the subject's head;
   a subject base plane generating unit for generating an anatomical base plane of the subject's head based on the conversion parameter and an anatomical base plane of the standard head; and
   a cross-sectional reconstruction unit for generating the cross-sectional image of the anatomical base plane of the subject's head based on the volume data of the subject's head and displaying said cross-sectional image on the display unit.

2. The medical cross-sectional image display apparatus according to claim 1, wherein:
   the apparatus further comprises a normal base plane generating unit for generating the anatomical base plane of the standard head as a normal base plane;
   wherein the normal base plane generating unit generates the normal base plane by inputting a standard voxel value to the voxel of the standard base plane out of a three-dimensional voxel data of the standard head.

3. The medical cross-sectional image display apparatus according to claim 1, wherein the conversion parameter is a linear transformation, a nonlinear transformation, an affine transformation or a Fourier transform, in which an error between a voxel value of the volume data of the subject's head and a voxel value of the volume data of the standard head becomes minimal.

4. The medical cross-sectional image display apparatus according to claim 2, wherein the conversion parameter is a linear transformation, a nonlinear transformation, an affine transformation or a Fourier transform, in which an error between a voxel value of the volume data of the subject's head and a voxel value of the volume data of the standard head becomes minimal.

5. The medical cross-sectional image display apparatus according to claim 3, wherein the subject's head and the standard head includes at least one of a cerebral parenchyma, a cranium bones and skin including facial parts outside of the cranium bones.

6. The medical cross-sectional image display apparatus according to claim 1, further comprising an angle adjusting unit for calculating angles of at least two axial directions of a plane of the medical cross-sectional image display apparatus and the anatomical base plane of the subject's head, rotating the anatomical base plane of the subject's head based on the angle and matching the anatomical base plane of the subject's head to the plane of the medical cross-sectional image display apparatus.

7. The medical cross-sectional image display apparatus according to claim 2, further comprising an angle adjusting unit for calculating angles of at least two axial directions of a plane of the medical cross-sectional image display apparatus and the anatomical base plane of the subject's head, rotating the anatomical base plane of the subject's head based on the angle and matching the anatomical base plane of the subject's head to the plane of the medical cross-sectional image display apparatus.

8. The medical cross-sectional image display apparatus according to claim 3, further comprising an angle adjusting unit for calculating angles of at least two axial directions of a plane of the medical cross-sectional image display apparatus and the anatomical base plane of the subject's head, rotating the anatomical base plane of the subject's head based on the angle and matching the anatomical base plane of the subject's head to the plane of the medical cross-sectional image display apparatus.

9. The medical cross-sectional image display apparatus according to claim 4, further comprising an angle adjusting unit for calculating angles of at least two axial directions of a plane of the medical cross-sectional image display apparatus and the anatomical base plane of the subject's head, rotating the anatomical base plane of the subject's head based on the angle and matching the anatomical base plane of the subject's head to the plane of the medical cross-sectional image display apparatus.

10. The medical cross-sectional image display apparatus according to claim 1, wherein the anatomical base plane includes a plane surface including an orbitomeatal line (OM LINE) connecting an orbital center and a center of an external auditory meatus, a plane surface including a supraorbitomeatal line (SM line) connecting a supraorbital margin and the center of the external auditory meatus and an infraorbitomeatal plane connecting an edge of the external auditory meatus and an infraorbital margin.

11. The medical cross-sectional image display apparatus according to claim 2, wherein the anatomical base plane includes a plane surface including an orbitomeatal line (OM LINE) connecting an orbital center and a center of an external auditory meatus, a plane surface including a supraorbitomeatal line (SM line) connecting a supraorbital margin and the center of the external auditory meatus and an infraorbitomeatal plane connecting an edge of the external auditory meatus and an infraorbital margin.

12. The medical cross-sectional image display apparatus according to claim 3, wherein the anatomical base plane includes a plane surface including an orbitomeatal line (OM LINE) connecting an orbital center and a center of an external auditory meatus, a plane surface including a supraorbitomeatal line (SM line) connecting a supraorbital margin and the center of the external auditory meatus and an infraorbitomeatal plane connecting an edge of the external auditory meatus and an infraorbital margin.

13. The medical cross-sectional image display apparatus according to claim 4, wherein the anatomical base plane includes a plane surface including an orbitomeatal line (OM LINE) connecting an orbital center and a center of an external auditory meatus, a plane surface including a supraorbitomeatal line (SM line) connecting a supraorbital margin and the center of the external auditory meatus and an infraorbitomeatal plane connecting an edge of the external auditory meatus and an infraorbital margin.

14. The medical cross-sectional image display apparatus according to claim 5, wherein the anatomical base plane includes a plane surface including an orbitomeatal line (OM LINE) connecting an orbital center and a center of an external auditory meatus, a plane surface including a supraorbitomeatal line (SM line) connecting a supraorbital margin and the center of the external auditory meatus and an infraorbitomeatal plane connecting an edge of the external auditory meatus and an infraorbital margin.

15. The medical cross-sectional image display apparatus according to claim 1, further comprising a cross-sectional edge setting unit for setting a first edge and a second edge of a region for reviewing the cross-sectional image based on the volume data of the subject's head.

16. The medical cross-sectional image display apparatus according to claim 1, wherein the cross-sectional image is an MRI (magnetic resonance imaging) image, a SPECT (Single Photon Emission Computed Tomography) or a PET (Positron Emission Tomography) image.

17. A method for displaying a cross-sectional image of a head on a display unit using a medical cross-sectional image connected to the display unit, comprising:
    a step for obtaining a conversion parameter indicating a difference in shape between a standard head and a subject's head based on a volume data of the standard head and the subject's head;
    a step for generating an anatomical base plane of the subject's head based on the conversion parameter and an anatomical base plane of the standard head; and
    a step for generating the cross-sectional image of the anatomical base plane of the subject's head based on the volume data of the subject's head and displaying said cross-sectional image on the display unit.

18. One or more non-transitory computer-readable storage media storing computer-executable instructions, the instructions when executed on one or more processors causing the one or more processors to:
    obtain a conversion parameter indicating a difference in shape between a standard head and a subject's head based on a volume data of the standard head and the subject's head;
    generate an anatomical base plane of the subject's head based on the conversion parameter and an anatomical base plane of the standard head; and generate the cross-sectional image of the anatomical base plane of the subject's head based on the volume data of the subject's head and displaying said cross-sectional image on the display unit.

19. The non-transitory computer-readable storage media according to claim 18, the instructions when executed on one or more processors causing the one or more processors to:

generate the anatomical base plane of the standard head as a normal base plane; and generate the normal base plane by inputting a standard voxel value to the voxel of the standard base plane out of a three-dimensional voxel data of the standard head.

* * * * *